(12) United States Patent
Rigaux et al.

(10) Patent No.: US 8,702,584 B2
(45) Date of Patent: *Apr. 22, 2014

(54) NEUROSTIMULATION METHOD TO INDUCE RELAXATION OR SLEEP

(75) Inventors: Pierre Rigaux, Liege (BE); Pierre-Yves Muller, Collonge Bellerive (CH)

(73) Assignee: Cefaly Technology SPRL, Herstal (BE)

( * ) Notice: Subject to any disclaimer, the term of this patent is extended or adjusted under 35 U.S.C. 154(b) by 217 days.

This patent is subject to a terminal disclaimer.

(21) Appl. No.: 13/101,495

(22) Filed: May 5, 2011

(65) Prior Publication Data

US 2011/0282129 A1  Nov. 17, 2011

Related U.S. Application Data

(60) Provisional application No. 61/333,884, filed on May 12, 2010.

(51) Int. Cl.
*A61M 21/00* (2006.01)
*A61N 1/00* (2006.01)

(52) U.S. Cl.
USPC ............................................. 600/26; 607/139

(58) Field of Classification Search
USPC ......................... 600/26–28; 607/46, 139–141
See application file for complete search history.

(56) References Cited

U.S. PATENT DOCUMENTS

| | | | |
|---|---|---|---|
| 5,540,734 A | 7/1996 | Zabara | |
| 6,954,668 B1 | 10/2005 | Cuozzo | |
| 8,380,315 B2 * | 2/2013 | DeGiorgio et al. | 607/45 |
| 2007/0276451 A1 | 11/2007 | Rigaux | |
| 2009/0210028 A1 | 8/2009 | Rigaux et al. | |

FOREIGN PATENT DOCUMENTS

WO  WO 2006/063417 A1  6/2006

* cited by examiner

*Primary Examiner* — John Lacyk
(74) *Attorney, Agent, or Firm* — Reinhart Boerner Van Deuren P.C.

(57) ABSTRACT

The present invention relates to a method for inducing relaxation or sleep comprising the steps of:
   placing electrodes in contact with the forehead skin in the supraorbital region;
   generating an electrical signal with a signal generator and applying said signal to the electrodes so as to produce external, i.e. non invasive, neurostimulation of the upper branch of the trigeminal nerve.

6 Claims, 2 Drawing Sheets

NEUROSTIMULATION METHOD TO INDUCE RELAXATION OR SLEEP

CROSS-REFERENCE TO RELATED PATENT APPLICATIONS

This patent application claims the benefit of U.S. Provisional Patent Application No. 61/333,884, filed May 12, 2010, the entire teachings and disclosure of which are incorporated herein by reference thereto.

FIELD OF THE INVENTION

The present invention pertains to the field of neurostimulation. Neurostimulation is a well-known technique which consists in using electrical impulses to generate action potential on nerves. The devices are usually implantable systems similar to pacemakers.

STX-Med Company has developed a specific device to apply external neurostimulation on the head in order to treat and prevent headaches and migraines. This technique is known as external cranial neurostimulation and is the subject of 2 patent submissions: WO 2006/063417 and US 2009/0210028.

PROBLEM TO BE SOLVED AND PRIOR ART

Generally neurostimulation devices, either implantable or external, are used to treat pain or to obtain muscle contractions. Some implantable systems are used as well for the stimulation of the vagus nerve against epilepsy. The vagal neurostimulation with the implantable systems is known to carry out some hypnotic effect and thus to induce sleep.

Traditional drug therapies intended to induce sleep are associated with drug side effects and tolerance leading sometimes to addiction.

Therefore using a safe technique without side effect to induce or enhance relaxation and/or sleep would be of great advantage. Neurostimulation of the vagus nerve has shown such property but it needs implantable systems, as the vagus nerve is not easily accessible with external neurostimulation.

U.S. Pat. No. 5,540,734 reports an invention in order to stimulate one or both of the trigeminal nerve and the glossopharyngeal nerve. However, this stimulation requires a surgically implantable system.

U.S. Pat. No. 6,954,668 reports an invention in order to stimulate the trigeminal nerve thanks to an apparatus for intra-oral stimulation. But such kind of apparatus is not convenient and easy to use for patients.

AIMS OF THE INVENTION

The invention aims at finding an easy and simple neurostimulation means that can induce relaxation and/or sleep.

Additionnally the invention aims at providing external neurostimulation.

SUMMARY OF THE INVENTION

The present invention relates to a method for inducing relaxation or sleep comprising the steps of:
placing electrodes in contact with the forehead skin in the supraorbital region;
generating an electrical signal with a signal generator and applying said signal to the electrodes so that to produce external, i.e. non invasive, neurostimulation of the upper branch of the trigeminal nerve.

Figure 1:
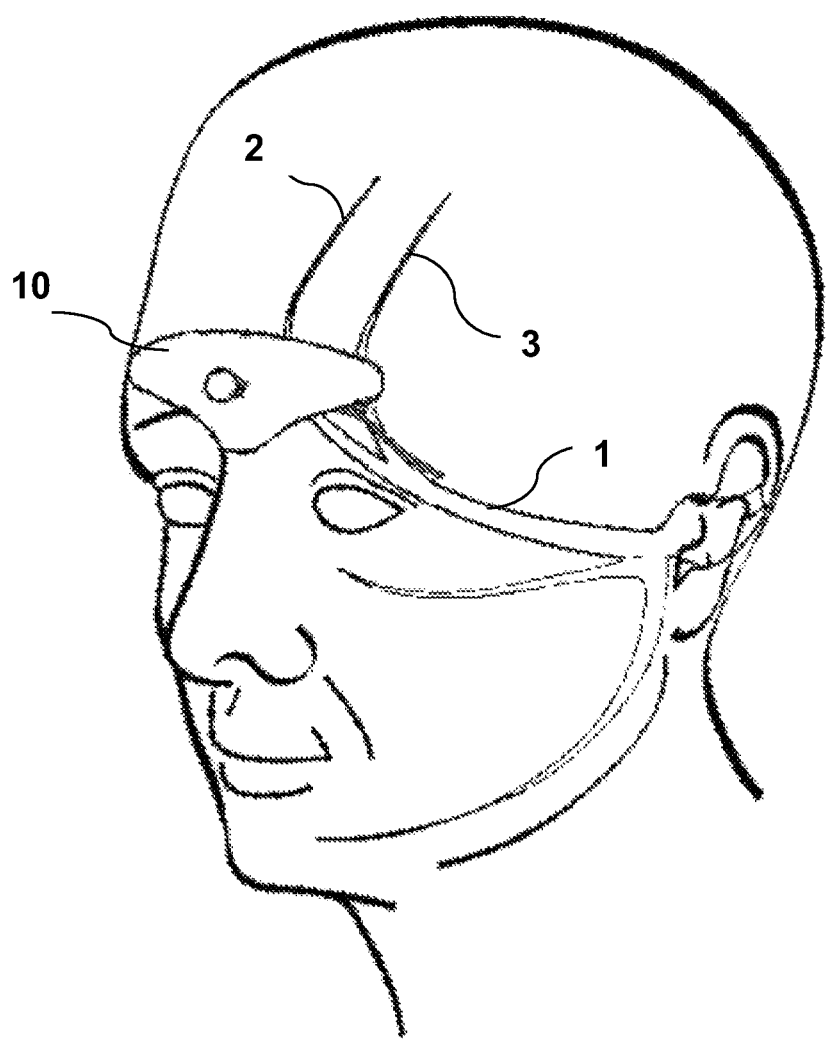

The method according to the invention may further comprise one or a suitable combination of the following characteristics:
the signal generator generates rectangular biphasic impulses having a impulse width between 10 and 500 µs, an impulse frequency between 1 and 150 Hz and an intensity between 1 and 25 mA, said intensity being progressively increased with a slope lower than 40 µA/sec;
the impulse width is about 250 µs;
the impulse frequency is about 120 Hz;
the method is carried out by use of two contact electrodes supported by an elongated symmetrical element, each electrode being in contact with a self-adhesive conductive gel substantially covering the face of the support intended to be applied to the skin (see FIG. 2);
the method is carried out with an electrode support having a shape and size selected so that to allow the excitation of the afferent paths of the supratrochlear and supraorbital nerves of the upper branch of the trigeminal nerve (see FIG. 1).

SHORT DESCRIPTION OF THE DRAWINGS

FIG. 1 schematically represents how to stimulate the afferent paths of the supratrochlear and supraorbital nerves of the upper branch of the trigeminal nerve.

Figure 2:
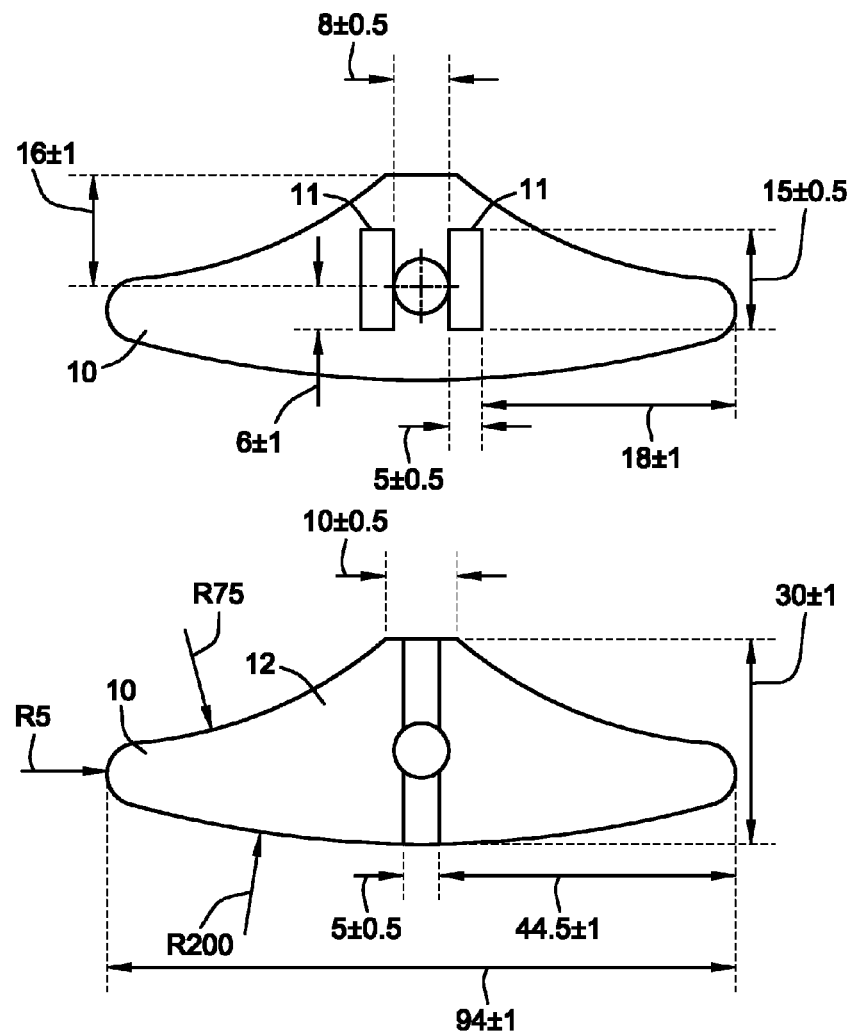

FIG. 2 represents more detailed views of a preferred embodiment, reducing constructively the invention to practice.

DETAILED DESCRIPTION OF THE INVENTION AND PREFERRED EMBODIMENTS

According to the present invention, the objective of inducing relaxation and/or sleep is specifically achieved by external, i.e. non invasive, neurostimulation of the trigeminal nerve 1 (supratrochlear nerve 2 and supraorbital nerve 3, see FIG. 1).

Cefaly® device (STX-Med, Herstal, Belgium) uses external supraorbital neurostimulation of the trigeminal nerve thanks to a specifically designed electrode applied on the forehead. A series of experiments and clinical tests was conceived to see if that could induce relaxation and sleep and to establish the appropriate parameters of neurostimulation in the upper branch of the trigeminal nerve.

The device used is a generator of electrical impulses connected with electrodes applied to the forehead skin. Preferred embodiments of this electrode are described in WO 2006/063417 and US 2009/0210028.

According to a preferred embodiment of the invention, the impulses emitted by the generator have the following specific characteristics:
rectangular biphasic impulses with an impulse width between 10 and 500 µs with an optimum at 250 µs;
impulse frequency between 1 and 150 Hz with an optimum at 120 Hz;
intensity between 1 and 25 mA;
progressive increase of the intensity with a slope lower than 40 µA/sec.

According to a preferred embodiment of the invention, the method is carried out with an electrode support 10 designed as a single self adhesive patch 12 with two conductive areas 11 which are the two electrodes. These two electrodes have the size as depicted in FIG. 2.

The invention claimed is:

1. Method for inducing relaxation or sleep comprising the steps of:
   placing electrodes in contact with the forehead skin in the supraorbital region;
   generating an electrical signal with a signal generator and applying said signal to the electrodes so as to produce external non invasive, neurostimulation of the upper branch of the trigeminal nerve.

2. Method according to claim 1, wherein the signal generator generates rectangular biphasic impulses having a impulse width between 10 and 500 μs, an impulse frequency between 1 and 150 Hz and an intensity between 1 and 25 mA, said intensity being progressively increased with a slope lower than 40 μA/sec.

3. Method according to claim 2, wherein the impulse width is about 250 μs.

4. Method according to claim 2, wherein the impulse frequency is about 120 Hz.

5. Method according to claim 1, wherein said method is carried out by use of two contact electrodes supported by an elongated symmetrical element, each electrode being in contact with a self-adhesive conductive gel substantially covering the face of the support intended to be applied to the skin.

6. Method according to claim 5, wherein the electrode support has a shape and size selected so as to allow the excitation of the afferent paths of the supratrochlear and supraorbital nerves of the upper branch of the trigeminal nerve.

* * * * *